(12) United States Patent
Zhao

(10) Patent No.: US 6,916,329 B1
(45) Date of Patent: Jul. 12, 2005

(54) OPTICAL/ELECTRICAL ACUPUNCTURE NEEDLE AND SYSTEM

(76) Inventor: Ruan Jin Zhao, 4440 Beauchamp Ct., Sarasota, FL (US) 34243

( * ) Notice: Subject to any disclaimer, the term of this patent is extended or adjusted under 35 U.S.C. 154(b) by 604 days.

(21) Appl. No.: 10/136,783

(22) Filed: Apr. 30, 2002

(51) Int. Cl.$^7$ ............................................. A61B 17/34
(52) U.S. Cl. ........................ 606/189; 607/116; 128/907
(58) Field of Search .................. 606/189; 607/116; 128/907

(56) References Cited

U.S. PATENT DOCUMENTS

| | | | |
|---|---|---|---|
| 3,773,049 A | * 11/1973 | Rabichev et al. ............... | 607/1 |
| 4,408,617 A | * 10/1983 | Auguste ...................... | 600/548 |
| 5,211,175 A | 5/1993 | Gleason | |
| 5,250,068 A | 10/1993 | Ideguchi et al. | |
| 5,843,074 A | 12/1998 | Cocilovo | |
| 6,306,160 B1 | 10/2001 | Nidetzky | |
| 6,346,103 B1 | 2/2002 | Korsec et al. | |
| 6,520,903 B1 | * 2/2003 | Yamashiro ...................... | 600/9 |
| 2002/0026225 A1 | * 2/2002 | Segal ........................... | 607/89 |

* cited by examiner

*Primary Examiner*—George Manuel
*Assistant Examiner*—Lenwood Faulcon
(74) *Attorney, Agent, or Firm*—Charles J. Prescott

(57) ABSTRACT

An optical/electrical transmission type acupuncture needle, controller and system for acupuncture treatment. The needle has a sharpened needle point one end configured for penetration into body tissue and a needle holder at the other end. The needle body is formed of a central optical transmission core, preferably an intermediate opaque non-conductive clad layer atop the core and an outer conductive layer positioned atop the clad layer, all of which are substantially coextensive one to another. The needle point is formed as a unit with the needle body by tapering, sharpening and highly polishing one end portion of the core sufficiently for body tissue penetration. The core carries light provided by a light source in the system controller which may simultaneously provide pulsed electricity carried by the outer conductive layer whereby pulsed light and electricity are transmitted into body tissue through the needle point.

5 Claims, 1 Drawing Sheet

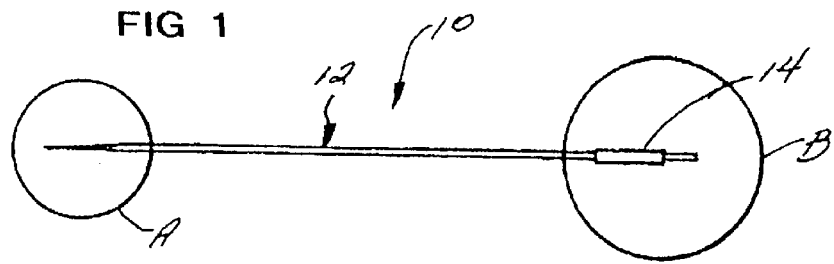
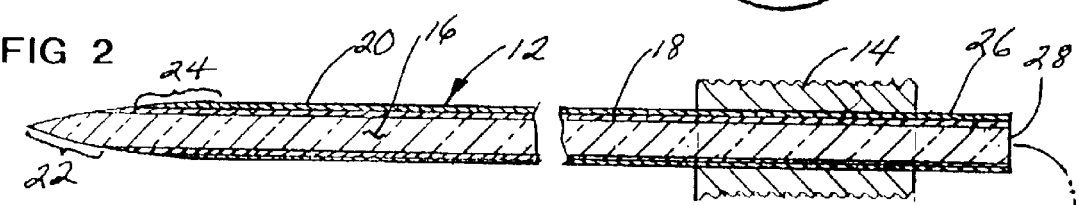
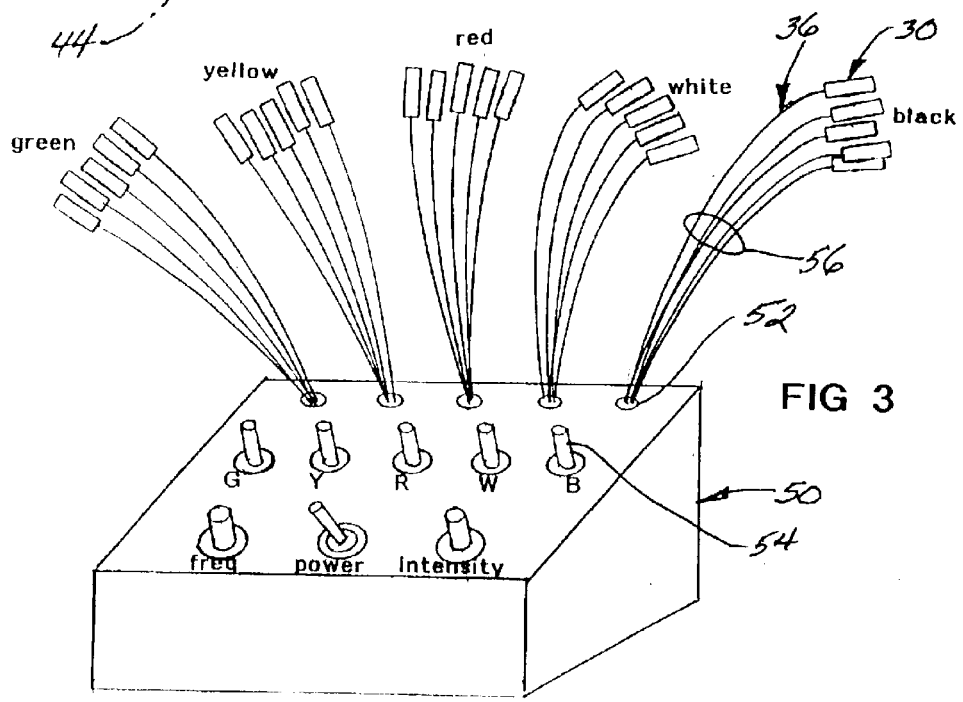

OPTICAL/ELECTRICAL ACUPUNCTURE NEEDLE AND SYSTEM

BACKGROUND OF THE INVENTION

Scope of Invention

This invention relates generally to the field of acupuncture medical treatment, and more particularly to an improved multi-function optical/electrical transmission type acupuncture needle, controller and system.

PRIOR ART

The ancient art of acupuncture medical treatment has been wholly embraced by western medical society. In this traditional treatment form, acupuncture needles formed of very thin cylindrical metal bodies are inserted at specific selected body tissue points, each acupuncture needle being sharpened at its distal end for easy insertion through the skin and into the body tissue by one of several techniques. One such insertion technique involves the rotation or twisting of the needle while applying pressure to the sharp needle tip. Another insertion mode is the striking of the needle tip against the body tissue after which it is tapped at its proximal or handle end lightly to achieve proper penetration. Another mode of needle insertion depends upon the use of a needle tube.

The insertion and presence of the distal tip portion of an acupuncture needle is, in and of itself, a significant medical therapeutic treatment which stimulates these critical acupuncture points throughout the human body.

To enhance the effectiveness of acupuncture treatment through needle insertion, three additional modes of energy enhancement are known to the acupuncturist or medical doctor utilizing this medical treatment technique. The first is in the form of heat applied to the proximal end of the needle adjacent to its handle portion. The use of MOXA placed onto the proximal end and then burned during the treatment after the needles have been placed is one well-known form of heat application.

A much more sophisticated utilization of heat is disclosed by Korsec in U.S. Pat. No. 6,346,103 in which a heating acupuncture needle is disclosed which incorporates an external energy source.

A second form of stimulation of the body tissue once the acupuncture needle has been placed properly is the application of pulsed low current and low voltage electricity. Conventional controllers are available which will apply an appropriate amount of pulsed electricity to the proximal end of the metallic acupuncture needle, the communication of which is accomplished typically by attachment of conventional alligator clips connected to the distal ends of each of the conductive wires leading from the controller.

A further enhancement of the beneficial effects of conventional acupuncture treatment is found in the utilization of light energy into the selected body tissue. An optical transmission type acupuncture needle is disclosed by Ideguchi in U.S. Pat. No. 5,250,068. This disclosure is directed to a light transmitting acupuncture needle which either has a hollow reflective surface or depends upon the use of a slender fiber optic inner core. A separate light-transmitting tip which is highly sharpened down to a radius measured in microns is attached to form the pointed end of this acupuncture needle.

Gleason, in U.S. Pat. No. 5,211,175 teaches an electro-acupuncture system for emitting high frequency magnetic energy pulses which are converted into pulses of electric current delivered into body tissue through a needle like electrode similar to that of an acupuncture needle.

The use of laser energy in both finding and treating acupuncture points is disclosed by Nidetzky in U.S. Pat. No. 6,306,160. This is self-contained unit which does not incorporate skin piercing features, but rather relies upon the intensity of the laser beam to penetrate through the skin to properly treat the desired body tissue point.

A therapeutic device using pulsed and colored light is disclosed by Cocilovo in U.S. Pat. No. 5,843,074. This disclosure teaches the utilization of pulsed non-coherent colored light stimulation for therapeutic effects. Pulsed/colored light is applied to local body areas or acupuncture macro or micro systems via an optical fiber extending through a pen-like hand piece.

The present invention provides an improved optical/electrical transmission type acupuncture needle, controller and system therefor which will selectively deliver not only the conventional acupuncture needle therapy to body tissue, but will also selectively apply pulsed electrical energy into the body tissue. The acupuncturist may also selectively apply one of a plurality of colored light energy sources for further enhanced body tissue and entire body treatment by acupuncture techniques. Thus, by using a single multi-function acupuncture needle in accordance with the teachings of this invention, the acupuncturist may also apply selected colored light energy and pulsed electrical energy utilizing the same system controller and acupuncture needle to accomplish any or all of these forms of acupuncture treatment.

BRIEF SUMMARY OF THE INVENTION

This invention is directed to an optical/electrical transmission type acupuncture needle and system for acupuncture treatment. The needle has a sharpened needlepoint one end configured for penetration into body tissue and a needle holder at the other end. The needle body is formed of a central optical transmission core, preferably an intermediate opaque non-conductive clad layer atop the core and an outer conductive layer positioned atop the clad layer, all of which are substantially coextensive one to another. The needle point is formed as a unit with the needle body by tapering, sharpening and highly polishing one end portion of the core sufficiently for body tissue penetration. The core carries light provided by a light source in the system controller which may simultaneously provide pulsed electricity carried by the outer conductive layer whereby pulsed light and electricity are transmitted into body tissue through the needle point.

It is therefore an object of this invention to provide an improved optical/electrical transmission type acupuncture needle for the selective treatment enhancement of either of these pulsed energy forms.

It is another object of this invention to provide a controller and system for use in conjunction with an improved optical/ electrical transmission type acupuncture needle for the selective additional treatment features of pulsed selective color energy and pulsed electrical energy into the body tissue being treated by the acupuncturist It is still another object of this invention to provide an economical to manufacture electrical/optical transmission type acupuncture needle which incorporates an optical fiber core extending entirely through the length of the needle and which is itself sharpened at the pointed end thereof for skin penetration and light energy delivery into body tissue.

In accordance with these and other objects which will become apparent hereinafter, the instant invention will now be described with reference to the accompanying drawings.

BRIEF DESCRIPTION OF THE DRAWINGS

FIG. 1 is a side elevation view of the present invention.

FIG. 2 is an enlarged cross sectional view of areas A and B of FIG. 1 and an exploded sectional view of the coupler and distal end of one light/electrical transmission cable as shown in FIG. 3.

FIG. 3 is a perspective view of the system controller and light/energy cables, each of which are attachable to the acupuncture needle of FIGS. 1 and 2.

DETAILED DESCRIPTION OF THE INVENTION

Referring now to the drawings, the invention generally includes an optical/electrical transmission type acupuncture needle 10 and a system controller 50 as seen in FIG. 3. The acupuncture needle 12 is generally formed of an elongated, cylindrical optical transmission core 16 formed of optical fiber for efficient light transmission therethrough. To prevent light energy from dispersing from the side walls of the optical fiber core 16, an opaque cladding layer 18 is formed over the entire exterior surface of the core 16. A third element of the preferred embodiment of the acupuncture needle 12 is in the form of a conductive outer layer 20 which is applied in the form of a thin film over the entire outer surface of the cladding layer 18.

The needle point 22 is sharpened into the shape of a conventional acupuncture needle as best seen in FIG. 2. The very tip of the needle point 22 is sharpened to a radius measured in microns for adequate skin and tissue penetration as the acupuncture needle 12 is inserted into the selected body tissue. This needle point 22 is highly polished as well so that all light energy passing through the core 16 will efficiently emanate therefrom into body tissue.

The outer conductive layer 20 is preferably also tapered along 24 so as to provide sufficient tapered sharpness of the acupuncture needle point for comfortable insertion thereof into body tissue and through the skin of the patient. A needle holder 14 which may be formed of any conventional material such as non-metallic PVC plastic having ribs or knurling on the outer surface. This needle holder 14 thus assists the acupuncturist in twisting and in proper positioning of the needle point 22 and additional portions of the acupuncture needle 12 adjacent thereto into the body tissue. The proximal end 28 of the core 16 is also highly polished so that light directed thereagainst would more completely be passed into the core 16 for emanation from the needle point 22.

Note that, although the opaque cladding 18, which is added for light energy containment within the core 16 and core strengthening itself, these aspects may be incorporated into the functional features described herebelow of the conductive outer layer 20 so that the two layers of cladding 18 and outer conductive layer 20 may be incorporated into a multi-task layer (not shown).

The system controller 50 as seen in FIG. 3 is in the form of a conventional metal or plastic housing having therewithin a source of electricity which may be one or more 9v d.c. batteries, an appropriate voltage transformer and a pulsed electricity generator and a pulsed light generator of multi-color nature (not shown).

Conventional means .(not shown) within the controller 50 generate selective colored light energy, namely the colors of green, yellow, red, white and black which have been found to be therapeutically beneficial to the human body.

Each of the optical/electrical transmission cables shown generally at 36 include a central optical fiber core 38 having a polished distal end at 44, a cladding layer 40 applied over the entire surface of the fiber optic core 38 for light containment, and an outer conductive layer 42 applied over substantially all of the cladding layer 40. The proximal end of each of these transmission cables 36 is connected as shown symbolically at 52 to the appropriate source of pulsed colored light energy and pulsed electricity so that, by actuating one of the switches 54, the appropriate light energy color will be available at the distal end 44 of each of the selected cable bundles 56. Likewise, the intensity and frequency of electrical energy may also be controlled by the switches indicated on the top face of the controller 50.

Permanently attached to each of the distal ends of each energy transmission cable 36 is a coupling 30 which includes a plastic tubular outer member 32 having an inner conductive layer 34. The conductive layer 34, when slidably engaged onto the proximal end portion 26 of the acupuncture needle 12 forms the electrical contact between the conductive outer layer 20 of the acupuncture needle 12 and the conductive outer layer 42 of the cable 36.

By this arrangement, the acupuncturist may selectively attach one of the cables 36 to the proximal end 26 of the acupuncture needle 12 after it has been positioned in selected body tissue and then be able to control the pulsed light energy and electric energy flowing through the needle point 22 and conductive layer portion 24 directly into the body tissue for enhanced remedial treatment.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. An optical/electrical transmission type acupuncture needle comprising:

an elongated slender needle body having a needle point at a first end portion thereof configured for penetration into selected body tissue and a needle holder provided at a second end portion of said needle body;

said needle body having a substantially uniform cross section over a substantially entire length thereof and being formed of a central optical transmission core, an intermediate opaque non-conductive clad layer positioned directly atop said core and an outer conductive layer positioned directly atop said clad layer, all of which are substantially coextensive one to another;

said needle point formed by tapering, sharpening and highly polishing said first end portion so that said first end portion of said core is sharpened sufficiently for body tissue penetration;

said core carrying light from a light source applied directly against a highly polished end surface of a second end of said core whereby light from the light source is transmitted through said core and emanates into body tissue from the tapered first end portion of said core.

2. An optical/electrical transmission type acupuncture needle comprising:

an elongated slender needle body having a needle point at a first end portion thereof configured for penetration into body tissue and a needle holder provided at a second end portion of said needle body;

said needle body having a substantially uniform cross section over a substantially entire length thereof and being formed of a central optical transmission core, an intermediate opaque non-conductive clad layer positioned directly atop said core and an outer conductive layer positioned directly atop said clad layer, all of which are substantially coextensive one to another;

said needle point formed by tapering, sharpening and highly polishing said first end portion so that said first end portion of said core is sharpened sufficiently for body tissue penetration;

said core carrying light from a light source applied directly against a highly polished end surface of a second end of said core whereby light from the light source is transmitted through said core and emanates into body tissue from the tapered first end portion of said core;

said conductive layer carrying electricity from an electric power source applied to a second end of said conductive layer whereby electricity from the electric power source is transmitted through said conductive layer and emanates into body tissue from the tapered first end portion of said conductive layer.

3. A system for delivering beneficial pulsed light energy of selected colors and pulsed electricity into selected body tissue via an optical/electrical transmission type acupuncture needle, said system comprising:

a plurality of said acupuncture needles each comprising:
an elongated slender needle body having a needle point at a first end portion thereof configured for penetration into body tissue and a needle holder provided at a second end portion of said needle body;
said needle body having a substantially uniform cross section over a substantially entire length thereof and being formed of a central optical transmission core, an intermediate opaque non-conductive clad layer positioned directly atop said core and an outer conductive layer positioned directly atop said clad layer, all of which are substantially coextensive one to another;
said needle point formed by tapering, sharpening and highly polishing said first end portion so that first end portion of said core is sharpened sufficiently for body tissue penetration;
said core carrying light from a light source applied directly against a highly polished end surface of a second end of said core whereby light from the light source is transmitted through said core and emanates into body tissue from the tapered first end portion of said core;
said conductive layer carrying electricity from an electric power source applied to a second end of said conductive layer whereby electricity from the electric power source is transmitted through said conductive layer and emanates into body tissue from the tapered first end portion of said conductive layer;

a system controller comprising:
a multi-color pulsed said light source and a pulsed said electric power source;
a plurality of elongated flexible leads each of which includes an optical transmission core having a proximal end thereof in light transmitting contact with one of the colors of pulsed light and surrounded by a conductive layer having a proximal end thereof in electrical contact with said electric power source;
a distal end of each of said flexible leads being connectable to said second end of one said acupuncture needle thereby selectively providing pulsed light of a selected color and/or pulsed electricity from said controller to said needle point and into the selected body tissue into which each said acupuncture needle has been inserted.

4. An optical/electrical transmission type acupuncture needle comprising:

an elongated slender needle body having a needle point at a first end portion thereof configured for penetration into body tissue and a needle holder provided at a second end portion of said needle body;

said needle body having a substantially uniform cross section over a substantially entire length thereof and being formed of a central optical transmission core and an opaque outer conductive layer positioned uniformly over said core;

said needle point formed by tapering, sharpening and highly polishing said first end portion so that said first end portion of said core is sharpened sufficiently for body tissue penetration;

said core carrying light from a light source applied directly against a highly polished end surface of a second end of said core whereby light from the light source is transmitted through said core and emanates into body tissue from the tapered first end portion of said core;

said conductive layer carrying electricity from an electric power source applied to a second end of said conductive layer whereby electricity from the electric power source is transmitted through said conductive layer and emanates into body tissue from the tapered first end portion of said conductive layer.

5. A system controller for delivering beneficial pulsed light energy of selected colors and pulsed electricity into selected body tissue via an optical/electrical transmission type acupuncture needle including:

an elongated slender needle body having a needle point at a first end portion thereof configured for penetration into body tissue and a needle holder provided at a second end portion of said needle body;

said needle body having a substantially uniform cross section over a substantially entire length thereof and being formed of a central optical transmission core, an intermediate opaque non-conductive clad layer positioned directly atop said core and an outer conductive layer positioned directly atop said clad layer, all of which are substantially coextensive one to another;

said needle point formed by tapering, sharpening and highly polishing said first end portion so that said first end portion of said core is sharpened sufficiently for body tissue penetration;

said core carrying light from a light source applied directly against a highly polished end surface of a second end of said core whereby light from the light source is transmitted through said core and emanates into body tissue from the tapered first end portion of said core;

said conductive layer carrying electricity from an electric power source applied to a second end of said conductive layer whereby electricity from the electric power source is transmitted through said conductive layer and emanates into body tissue from the tapered first end portion of said conductive layer;

said system controller comprising:

a multi-color pulsed said light source and a pulsed said electric power source;

a plurality of elongated flexible leads each of which includes an optical transmission core having a proximal end thereof in light transmitting contact with one of the colors of pulsed light and surrounded by a conductive layer having a proximal end thereof in electrical contact with said electric power source;

a distal end of each of said flexible leads being connectable to said second end of one said acupuncture needle thereby selectively providing pulsed light of a selected color and/or pulsed electricity from said controller to said needle point and into the selected body tissue into which each said acupuncture needle has been inserted.

* * * * *